(12) United States Patent
Passadore et al.

(10) Patent No.: US 8,968,273 B2
(45) Date of Patent: Mar. 3, 2015

(54) CATHETER SET

(71) Applicant: Medical Service GmbH, Bad Liebenzell (DE)

(72) Inventors: Riccardo Passadore, Paderno Dugnano (IT); Bernhard Hiesch, Schömberg (DE)

(73) Assignee: Medical Service GmbH, Bad Liebenzell (DE)

( * ) Notice: Subject to any disclaimer, the term of this patent is extended or adjusted under 35 U.S.C. 154(b) by 0 days.

(21) Appl. No.: 13/657,076

(22) Filed: Oct. 22, 2012

(65) Prior Publication Data

US 2013/0144271 A1    Jun. 6, 2013

(30) Foreign Application Priority Data

Oct. 21, 2011   (DE) .................... 20 2011 107 025 U

(51) Int. Cl.
| | | |
|---|---|---|
| *A61M 25/00* | (2006.01) | |
| *A61M 25/01* | (2006.01) | |
| *A61M 25/08* | (2006.01) | |
| *A61F 5/44* | (2006.01) | |
| *B65D 83/00* | (2006.01) | |

(52) U.S. Cl.
CPC ............ *A61M 25/0017* (2013.01); *B65D 83/00* (2013.01); *A61M 2210/1078* (2013.01); *A61M 25/013* (2013.01); *A61M 25/002* (2013.01); *A61M 25/0111* (2013.01); *A61F 5/44* (2013.01)
USPC ............................ 604/544; 604/540; 604/264

(58) Field of Classification Search
CPC .................. A61M 2210/1078; A61M 25/0017; A61M 25/0111; A61M 25/013; A61M 1/0019; A61M 2210/1085; A61M 2210/1089; A61M 2210/1092; A61M 2210/1096; A61M 25/002; A61M 25/0041; A61M 27/008; A61M 25/0113; A61F 5/44; B65D 83/00; A61B 2017/00287; B65B 27/10; B65B 27/06
USPC ............ 604/540, 544, 328, 93.01, 158, 159, 604/163, 164.01, 167.06, 171, 172, 177
See application file for complete search history.

(56) References Cited

U.S. PATENT DOCUMENTS

| | | | | |
|---|---|---|---|---|
| 2,856,932 A | * | 10/1958 | Griffitts ........................ | 604/171 |
| 3,001,565 A | * | 9/1961 | Beach ........................... | 604/326 |
| 3,556,294 A | * | 1/1971 | Walck et al. .................. | 206/210 |
| 3,648,704 A | * | 3/1972 | Jackson ........................ | 604/172 |
| 3,762,399 A | * | 10/1973 | Riedell ........................ | 600/580 |
| 4,204,527 A | * | 5/1980 | Wu et al. ........................ | 600/575 |
| 4,230,115 A | | 10/1980 | Walz, Jr. et al. | |
| 5,147,341 A | * | 9/1992 | Starke et al. .................. | 604/349 |
| 5,149,326 A | * | 9/1992 | Woodgrift et al. ............ | 604/163 |

(Continued)

FOREIGN PATENT DOCUMENTS

| | | |
|---|---|---|
| EP | 1641510 B1 | 12/2008 |
| WO | 03/008028 A2 | 1/2003 |

*Primary Examiner* — Adam Marcetich
(74) *Attorney, Agent, or Firm* — Baker Hostetler LLP

(57) ABSTRACT

The present invention relates to a catheter set with a catheter, which has a catheter shaft; a package, which encompasses at least partially the catheter and which has an slide-out removal opening for the catheter; and a gripping aid, which is arranged in the package and which is movable on the catheter shaft, whereby the gripping aid is attached to the package and spaced a distance to the slide-out removal opening in such a manner that package material that can be pushed together is arranged between the gripping aid and the slide-out removal opening.

15 Claims, 2 Drawing Sheets

(56) References Cited

U.S. PATENT DOCUMENTS

| | | | |
|---|---|---|---|
| 5,454,798 A | 10/1995 | Kubalak et al. | |
| 6,009,998 A * | 1/2000 | Webinger | 206/364 |
| 6,053,905 A | 4/2000 | Daignault, Jr. et al. | |
| 6,578,709 B1 | 6/2003 | Kavanagh et al. | |
| 7,476,223 B2 | 1/2009 | McBride | |
| 2002/0103467 A1* | 8/2002 | Kubalak | 604/327 |
| 2003/0018302 A1* | 1/2003 | Kavanagh et al. | 604/172 |
| 2003/0018322 A1* | 1/2003 | Tanghoj et al. | 604/544 |
| 2005/0070882 A1* | 3/2005 | McBride | 604/544 |
| 2006/0163097 A1* | 7/2006 | Murray et al. | 206/364 |
| 2009/0043287 A1* | 2/2009 | Mosler et al. | 604/544 |
| 2009/0204106 A1* | 8/2009 | Golden | 604/544 |
| 2010/0312203 A1* | 12/2010 | House | 604/322 |
| 2012/0239005 A1* | 9/2012 | Conway et al. | 604/544 |

\* cited by examiner

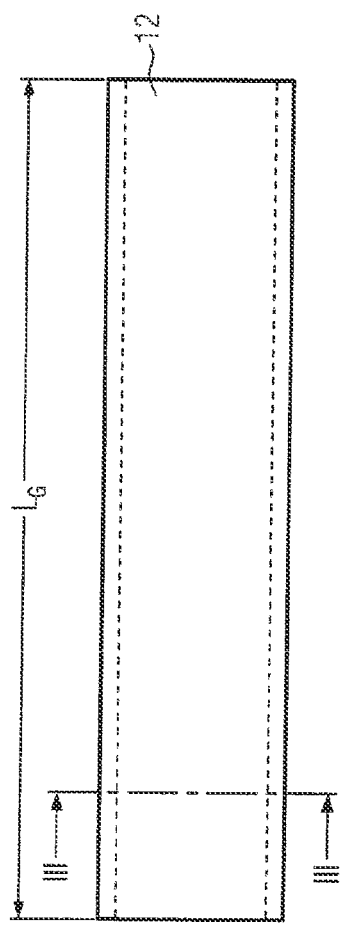
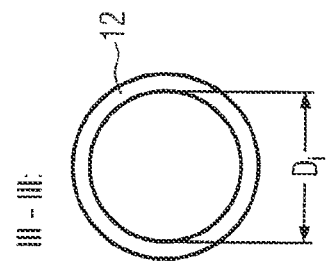
FIG. 2a
FIG. 2b

CATHETER SET

CROSS-REFERENCE TO RELATED APPLICATION

This application claims priority to foreign German patent application No. DE 202011107025.9, filed on Oct. 21, 2011.

FIELD OF THE INVENTION

The present invention relates to a catheter set with a catheter, which has a catheter shaft; a package, which encompasses at least partially the catheter and which has a slide-out removal opening for the catheter; and a gripping aid, which is arranged in the package and which is movable on the catheter shaft.

BACKGROUND

Such catheter sets are used, for example, for intermittent catheterisation. Intermittent catheterisation is the repeated emptying of the urinary bladder by means of a thin, single-use catheter. In principle, the single-use catheterisation of the urinary bladder should be carried out aseptically, i.e., with the use of sterile materials, disinfection of the urethra opening, use of a sterile lubricant and the sterile insertion of the catheter. For simple performance of intermittent catheterisation, there are a number of purchasable sets that contain all necessary individual parts. Because the users are often restricted in their movement, simple handling is particularly important for such sets.

From EP 1 641 510, a urinary catheter set is known that comprises a sterile package with a urinary catheter arranged in it. A collar is arranged on the catheter shaft of the urinary catheter. The collar is movable along the catheter shaft. When the urinary catheter is used, the package is opened and the urinary catheter is removed. The user can grip the urinary catheter on the collar thereby, so that sterile handling of the catheter is possible. Because the catheter is removed from the sterile package for use, however, there is always a risk of contamination.

U.S. Pat. No. 5,454,798 also shows a urinary catheter set with a urinary catheter that is arranged in a sterile package. Each end of the package is closed with sealing seams. At the front end of the package, i.e., at the end at which the catheter is removed from the package, an insertion aid is arranged on the catheter. The rear end of the insertion aid is attached to the package by means of the front sealing seam. The insertion aid encompasses the catheter tip and forms a slide-out removal opening for the catheter. The package is extended beyond the front sealing seam and closed by means of a third sealing seam so that the catheter tip is also packaged in a sterile manner. A bellows is arranged between the rear end of the insertion aid, which is fixed in place in the sealing seam, and the front end of the insertion aid, which encompasses the catheter tip. In order to insert the catheter, the user grips the two ends of the insertion aid and pulls the catheter out of the package by means of gripping and releasing the two ends and folding the bellows in and out. The insertion aid is consequently a relative complicated construction.

U.S. Pat. No. 6,578,709 B1 shows a further urinary catheter set with a sterile package, in which a catheter and a wetting device are enclosed. The wetting device is formed as a wetting chamber that has on one end an opening at which the catheter can be slid outwards for use. The housing of the wetting chamber is used as a gripping aid during the insertion of the catheter. When inserting the catheter, the user therefore holds the housing with one hand and grips the other end of the catheter through the package with the fingers of the other hand. Then the hand that holds the catheter through the package is moved forwards, towards the wetting chamber, and the catheter is slid outwards through the opening in the wetting chamber. The wetting chamber consequently forms the gripping aid and the slide-out removal opening for the catheter.

U.S. Pat. No. 4,230,115 also shows a catheter set with a sealed package in which a catheter, preferably a urinary catheter, is arranged. Formed in the package is a tapering in which a tube-shaped gripping aid is arranged. The tip of the catheter is arranged in the gripping aid. Two chambers are formed in the package by the tapering in the package: A first chamber, which is formed between a first end of the package and the gripping aid and which has a predetermined breaking point, and a second chamber formed between the gripping aid and the second end of the package, in which the catheter is arranged. For the insertion of the catheter, the package is opened at the predetermined breaking point and a lubricant is inserted into the first chamber. Then the penis is inserted into this first chamber. As a result, the urethra is automatically aligned with the hole of the gripping aid. The catheter is then inserted through the gripping aid and into the urethra. The gripping aid consequently forms the slide-out removal opening for the catheter.

Still another urinary catheter set is shown in U.S. Pat. No. 6,053,905. This urinary catheter set also comprises a package in which the urinary catheter is arranged. A slide-out removal opening for the catheter is arranged at one end of the package. In front of this catheter slide-out removal opening is a lubricant chamber through which the catheter is pushed during use and wetted with lubricant. A gripping aid is attached at the outlet of the lubricant chamber, i.e., of the catheter slide-out removal opening. Moreover, two parallel sealing seams that form a catheter guide can be provided in the package.

WO 03/008028 also discloses a catheter set with a package in which a urinary catheter is arranged. A component that forms a lubricant chamber, a gripping aid and a slide-out removal opening is attached in the closing-off sealing seam of the package. Here it is also described that for the insertion of the catheter, the user grips the front end of the catheter with the help of the gripping aid and grips the rear end of the catheter through the walls of the packages and moves the catheter in the direction of the slide-out removal opening of the package.

SUMMARY OF THE INVENTION

The object of the invention is to improve further catheter sets that are already known. The handling of the catheter sets is to be simplified further. Moreover, simple and economical manufacture is desired.

According to the invention, this object is solved by attaching the gripping aid to the package, spaced a distance from the slide-out removal opening such that package material that can be pushed together is arranged between the gripping aid and the slide-out removal opening.

Particularly if the catheter or catheter shaft has been coated with lubricant, it has a very slippery surface and is therefore difficult to grip. Easy gripping of the catheter is possible due to the gripping aid fixed to the package. The catheter cannot slip away. The distance between the gripping aid and the slide-out removal opening in the package simplifies the insertion of the catheter. Because the gripping aid is arranged on the package and consequently remains in the package during use, sterile handling is guaranteed.

In a preferred development, it can be provided that the gripping aid is formed as a flexible sleeve. The sleeve can be a piece of hose made, for example, of PVC. This makes possible a very simple arrangement of the gripping aid. If the flexible sleeve is gripped, the catheter shaft can be clamped by means of pressing the sleeve shut and it can be simply slid forwards in the package. The gripping of the catheter shaft is facilitated in this way. The sleeve can be a closed or a slotted sleeve. Because the catheter shaft is encompassed by the sleeve across the entire circumference, a firm grip is possible and the catheter shaft cannot slide sideways out of the sleeve.

Preferably it can furthermore be provided that the slide-out removal opening is formed in one package end. In this way, a very simple arrangement of the slide-out removal opening is possible.

Advantageously, it can be provided that the slide-out removal opening is formed by a stiffening in the package. Consequently, for example, a tube piece can be attached to the package, and it can form the slide-out removal opening. In this way, two fixed gripping points for the catheter shaft are formed, with one being the gripping aid and the other the tube piece that forms the slide-out removal opening. This makes it easier to pull the catheter shaft out of the package and therefore to insert the catheter.

A further development can provide that the distance between the slide-out removal opening and the gripping aid amounts to at least one-fourth of the length of the catheter shaft. It has been seen that easy insertion of the catheter is possible with this length.

Furthermore, it can be provided that the gripping aid is fixed in place in the package by at least one sealing seam. In this way, very simple attachment of the gripping aid to the package is possible. The manufacture of the catheter is simplified. In order to achieve a secure attachment, preferably it can be provided that the gripping aid is encompassed by two clamp-like sealing seams that lie opposite each other.

Advantageously, it can furthermore be provided that the length of the gripping aid amounts to at least 10% of the length of the catheter shaft. With this length, it is ensured that the user can grip the gripping aid easily.

Still another arrangement can provide that the inside diameter of the gripping aid amounts to roughly 1.5 times to 3 times the catheter diameter. The inside diameter of the gripping aid is consequently sufficiently large in order to allow the catheter shaft to be drawn through easily. Moreover the inside diameter of the gripping aid is not too large, so that good fixation of the catheter shaft in the gripping aid is made possible when it is pressed together.

It can furthermore be provided that the catheter has on its end that faces away from the slide-out removal opening a limit stop and that the inside diameter of the gripping aid is greater than the outside diameter of the limit stop. The limit stop can consequently also be drawn through the gripping aid.

The diameter of the slide-out removal opening is advantageously smaller than the outside diameter of the limit stop. The catheter can consequently not be drawn completely out of the package. The catheter end is held back in the package and it seals off the slide-out removal opening. Consequently the contents cannot run out of the package and good hygiene is guaranteed. The limit stop can be pressed against the slide-out removal opening by means of the gripping aid in order to ensure the sealing function.

In a further preferred embodiment, it can be provided that the package is formed as a urine collection container. The catheter set is consequently a closed system, so that good hygiene is made possible.

Advantageously, it can be provided that the gripping aid is arranged in the urine collection container. The gripping aid consequently remains in the package, so that contamination is avoided.

Preferably the slide-out removal opening can be reclosed. After the use of the catheter set, the catheter is guided back into the package and the slide-out removal opening is closed again so that good hygiene is guaranteed.

It can furthermore be provided that a sachet that contains a lubricant is arranged in the package. This lubricant can be any kind of liquid that reduces the friction on the surface of the catheter shaft and that facilitates the insertion of the catheter. All components necessary for the use of the catheter are arranged completely in the package, so that simple handling is facilitated. By pressing together the sachet, the lubricant is released in the package and the catheter is thereby wetted and consequently made ready for use.

A further arrangement can provide that the catheter has a hydrophilic coating. This further facilitates the use of the catheter and minimises the sliding friction during insertion.

In a particularly preferred embodiment, the gripping aid can be arranged on a long side of the package. In this way, the activation of the catheter by means of the lubricant is optimised.

BRIEF DESCRIPTION OF THE DRAWINGS

In the following, the invention is described in more detail on the basis of drawings. Shown are:

FIG. 2a gripping aid of the catheter set shown in FIG. 1, and

FIG. 2b sectional view through the gripping aid shown in FIG. 2 along the line III-III.

DETAILED DESCRIPTION

Figure 1:
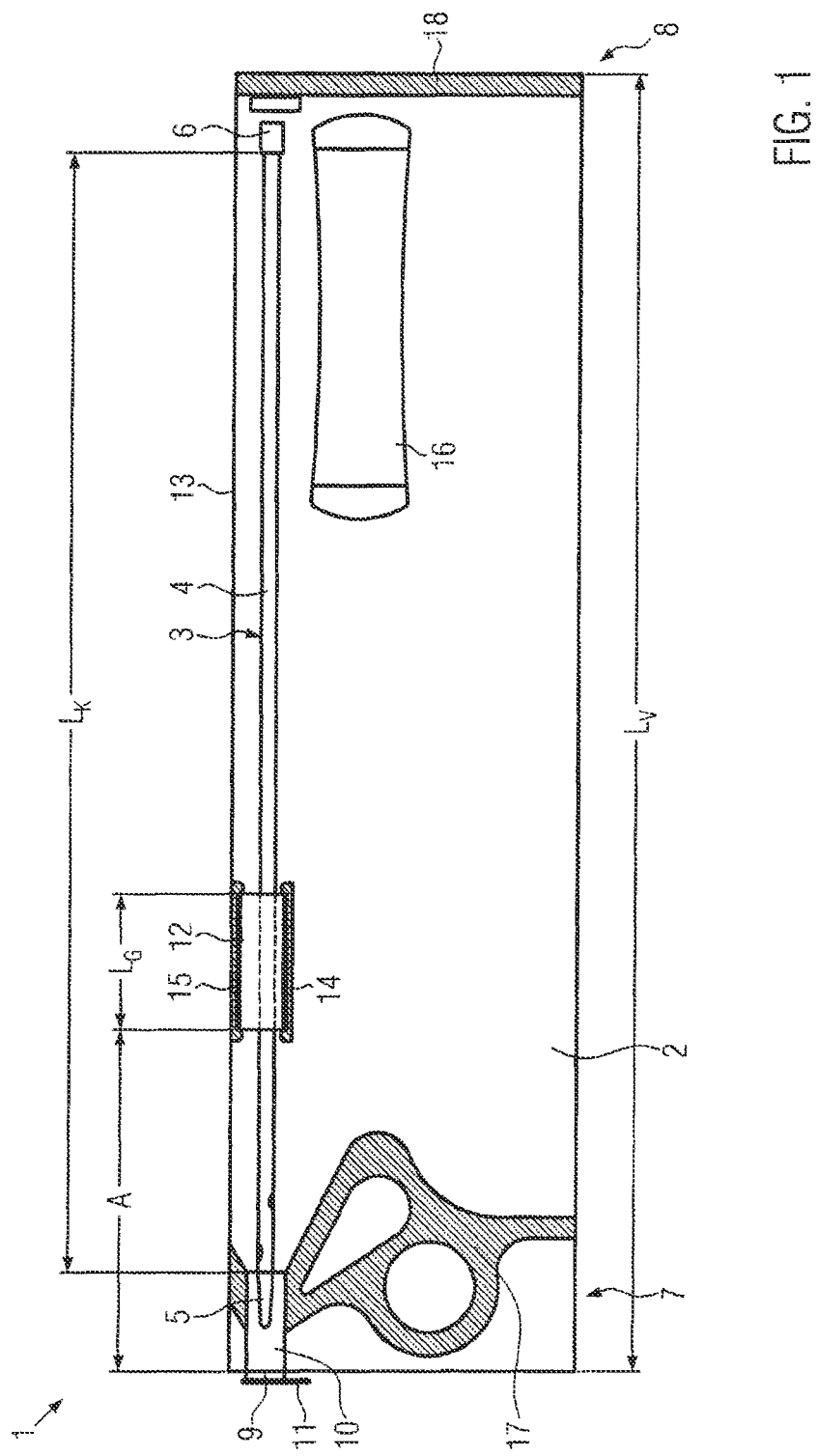
FIG. 1 catheter set.

FIG. 1 shows a catheter set 1. The catheter set 1 comprises a package 2 and a catheter 3 arranged in the package 2. The catheter 3 is sterilised with the package 2. The sterility of the catheter 3 can be ensured by the package 2 until its use.

The urinary catheter 3 has a catheter shaft 4, a catheter tip 5 and, on its end situated opposite the catheter tip 5, a limit stop 6. The urinary catheter 3 is arranged completely in the package 2. The package has an elongated shape. Other shapes are also conceivable, however. Preferably a PE foil is used as the material for the package 2. In the depicted example, the package 2 is manufactured from a foil hose. The length $L_V$ of the package 2 is somewhat greater than the total length of the catheter 3. The catheter 3 is arranged in the package 2 in an elongated manner. The package is closed by sealing seams 17, 18 at the front end 7 of the package 2, i.e., at the end on which the catheter tip 5 is arranged, and on the rear end 8 of the package 2, i.e., on the end on which the limit stop 6 of the catheter 3 is arranged. A slide-out removal opening 9 is formed in the front sealing seam 17. For this purpose, a tube piece 10 that forms the slide-out removal opening 9 is attached in the sealing seam 17. The tube piece 10 has a cover 11 so that it can be reclosed. The catheter tip 5 is arranged in the tube piece 10 and consequently adjacent to the slide-out removal opening 9.

A gripping aid 12 is located in the interior of the package 2. The gripping aid 12 is formed by a flexible sleeve, for example, a hose piece. The gripping aid 12 is arranged on a long side 13 of the package. The gripping aid 12 is attached to the package 2 by means of two sealing seams 14, 15 that are situated opposite each other. The sealing seams 14, 15 are formed in a clamp-like manner and extend along the length $L_G$ of the gripping aid 12. On the front and on the rear end of the gripping aid 12, the sealing seams 14, 15 project beyond the gripping aid 12 a bit inwards. The catheter 3 is guided through the gripping aid 12 so that the gripping aid 12 encompasses the catheter shaft 4. The inside diameter of the gripping aid 12 is greater than the outside diameter of the catheter shaft 4 and the outside diameter of the limit stop 6. The gripping aid 2 is consequently arranged such that it can be moved on the catheter shaft 4, i.e., the gripping aid 12 can be moved with respect to the catheter shaft 4. The diameter of the slide-out removal opening 9 is less than the outside diameter of the limit stop 6.

The gripping aid 12 is arranged such that it is spaced at a distance to the slide-out removal opening 9. As a result, package material is arranged between the slide-out removal opening 9 and the gripping aid 12. The package material can be pushed together, so that the gripping aid 12 and the slide-out removal opening 9 can be moved towards each other. This can be seen clearly in FIG. 1. The distance A between the slide-out removal opening 9 and the front end of the gripping aid 12 amounts to at least one-fourth of the length of the catheter shaft $L_K$. The distance A preferably amounts to between one-fourth and one-third of the length $L_K$.

Furthermore, a sachet 16 that contains a lubricant is arranged in the package 2. Depending on the arrangement of the catheter 3 or of the catheter shaft 4, the lubricant can be a saline solution, water or a lubricating gel or any other liquid that reduces the friction between the catheter and the urethra. The package 2 is formed as a urine collection container.

FIG. 2a shows the gripping aid 12 from FIG. 1. The gripping aid 12 is sleeve-shaped and is formed by a soft hose piece. Preferably PVC is used as the material for the hose. The length of the gripping aid $L_G$ amounts to at least 10% of the length of the catheter shaft $L_K$. As a result, the gripping aid can be gripped easily by a user.

FIG. 2b shows a cross-section through the gripping aid 12 from FIG. 1. The gripping aid 12 has the shape of a hollow cylinder. The inside diameter $D_I$ of the gripping aid 12 amounts to roughly 1.5 to 3 times the catheter diameter. The depicted gripping aid 12 is closed along the entire circumference. It can also be provided to use a slotted sleeve as a gripping aid.

The cover 11 of the tube piece 10 and consequently the slide-out removal opening 9 is opened in order to use the catheter set 1. The user grips both the tube piece 10 and the gripping aid 12. The catheter shaft 4 is gripped firmly when the user presses together the gripping aid 12. The gripping aid 12 is then moved in the direction of the slide-out removal opening 9 and consequently the catheter tip 5 is slid out of the package 2 through the tube piece 10. The package material located between the slide-out removal opening 9 and the gripping aid 12 is thereby pushed together. The catheter tip 5 can now be inserted into the urethra. Now the tube piece 10, which defines the slide-out removal opening 9, is pressed together and the grip on the gripping aid 12 is released. The gripping aid 12 can be guided towards the back along the catheter shaft 4. In this way, the package material located between the gripping aid 12 and the slide-out removal opening 9 can be extended again. The gripping aid 12 is now pressed together again and moved in the direction of the slide-out removal opening 9, and at the same time, the grip on the tube piece 10 is loosened, so that the catheter shaft 4 is slid out of the package 2. By repetition of this process, the catheter 3 is slid out of the package 2 to reach the desired length. Preferably this takes place until the limit stop 6 lies on the tube piece 10. The limit stop 6 can be pressed against the tube piece 10 by means of the gripping aid 12 in such a manner that a tight connection results. Now urine can flow into the package 2 without fluid escaping. After the completion of the process, the catheter 3 is pulled back into the package 2 and the slide-out removal opening 9 is closed again by means of the cover 11.

The invention claimed is:

1. A catheter set comprising: a catheter, which has a catheter shaft; a package, which encompasses at least partially the catheter and which has an slide-out removal opening for the catheter; and a gripping aid, which is arranged entirely in the package and which is movable on the catheter shaft, wherein the gripping aid is attached to the package and spaced a distance to the slide-out removal opening in such a manner that package material that can be pushed together is arranged between the gripping aid and the slide-out removal opening,
   wherein the gripping aid is formed as a flexible sleeve having a hollow shape, and
   wherein the gripping aid is arranged along on a long side of the package.

2. The catheter set according to claim 1, wherein the slide-out removal opening is formed in a package end.

3. The catheter set according to claim 1, wherein the slide-out removal opening is formed by a stiffening in the package.

4. The catheter set according to claim 1, wherein a distance between the slide-out removal opening and the gripping aid amounts to at least one-fourth of a length of the catheter shaft.

5. The catheter set according to claim 1, wherein the gripping aid is fixed in place in the package by at least one sealing seam.

6. The catheter set according to claim 1, wherein a length of the gripping aid amounts to at least 5% of a length of the catheter shaft.

7. The catheter set according to claim 1, wherein an inside diameter of the gripping aid is about 1.5 times to 3 times the catheter diameter.

8. The catheter set according to claim 1, wherein the catheter has a limit stop on its end that faces away from the slide-out removal opening and an inside diameter of the gripping aid is greater than the outside diameter of the limit stop.

9. The catheter set according to claim 8, wherein the diameter of the slide-out removal opening is less than the outside diameter of the limit stop.

10. The catheter set according to claim 1, wherein the package is formed as a urine collection container.

11. The catheter set according to claim 10, wherein the gripping aid is arranged in the urine collection container.

12. The catheter set according to claim 1, wherein the slide-out removal opening can be reclosed.

13. The catheter set according to claim 1, wherein a sachet that contains a lubricant is arranged in the package.

14. The catheter set according to claim 1, wherein the catheter shaft has a hydrophilic coating.

15. The catheter set according to claim 1,
   wherein an inside diameter of the gripping aid is about 1.5 times to 3 times the catheter diameter, and
   wherein a length of the gripping aid amounts to at least 10% of a length of the catheter shaft, and
   wherein a distance between the slide-out removal opening and the gripping aid amounts to at least one-fourth of a length of the catheter shaft.

* * * * *